(12) United States Patent
Nakanishi

(10) Patent No.: US 6,315,559 B1
(45) Date of Patent: Nov. 13, 2001

(54) PROPHY HEAD

(75) Inventor: Takasuke Nakanishi, Kanuma (JP)

(73) Assignee: Nakanishi Inc., Tochigi-ken (JP)

( * ) Notice: Subject to any disclaimer, the term of this patent is extended or adjusted under 35 U.S.C. 154(b) by 0 days.

(21) Appl. No.: 09/515,646

(22) Filed: Feb. 29, 2000

(30) Foreign Application Priority Data

Mar. 3, 1999 (JP) .................................................. 11-055194

(51) Int. Cl.[7] .................................. A61C 3/06; A61C 1/16
(52) U.S. Cl. ............................................. 433/125; 433/116
(58) Field of Search ...................................... 433/116, 125

(56) References Cited

U.S. PATENT DOCUMENTS

| | | | |
|---|---|---|---|
| 2,791,835 | * 5/1957 | Staunt | 433/116 |
| 5,642,995 | * 7/1997 | Bailey | 433/116 |
| 5,676,542 | 10/1997 | Lingenhole et al. | 433/115 |

FOREIGN PATENT DOCUMENTS

| | | |
|---|---|---|
| 54-69699 | 5/1979 | (JP) . |
| 8-66411 | 3/1996 | (JP) . |

* cited by examiner

*Primary Examiner*—John J. Wilson
(74) *Attorney, Agent, or Firm*—Keil & Weinkauf

(57) ABSTRACT

Prophy head for a handpiece used in dentistry. The prophy head has a rotating shaft which holds a polishing member, a bearing for supporting the shaft, a housing for retaining the bearing, and a rotary dust control device which rotates with the shaft and prevents intrusion of contaminants. The dust control device has a surface extending radially outwardly from the shaft and downwardly beyond the lower end of the housing, and a surface in close proximity to the inner surface of the lower end of the housing.

4 Claims, 5 Drawing Sheets

PROPHY HEAD

FIELD OF ART

This invention relates to a prophy head which is a head portion of a prophy handpiece for use in removing dental plaque, dental calculus, dental stains, and the like, settled on dental surfaces and interdental spaces, as well as in polishing dental surfaces and interdental spaces.

BACKGROUND OF THE INVENTION

A prophy handpiece equipped with a prophy head is for use in removing dental plaque, dental calculus, dental stains, and the like, settled on dental surfaces and interdental spaces, or in polishing dental surfaces after removal of dental calculus and the like by a scaler, or after patch-up of the dental surfaces or the like with a photo-polymerized resin.

FIG. 5 is a cross sectional view showing the construction of a conventional prophy head 50, which is coupled to a sheath, not shown, having a motor accommodated therein. A housing section 51 of the prophy head 50 is formed of a head portion 51a and a mouthpiece 51b, and having a shaft (screw shaft) 52 therein. When it is used, a polishing brush 1 like one shown in FIG. 1 is attached to the shaft 52. In the thus formed prophy head 50, a rotary output from the motor accommodated in the sheath is transmitted via driving force transmitting means consisting of a driving shaft 53a, a driving gear 53b, and an output shaft gear 53c, to the shaft 52, and the thus transmitted output rotates the brush 1 with an abrasive applied thereto, to thereby carry out required polishing work. In place of the brush 1, a rubber cup 2 like one shown in FIG. 2 may be used.

When the prophy head is used, contaminants such as tooth debris, blood and/or saliva can easily enter the interior of the head portion 51a through a gap between the shaft 52 and the mouthpiece 51b. In other words, the gap can become a contaminant intrusion port. If the entered contaminants are allowed to accumulate therein, a bearing 54 and the gear 53c can be disadvantageously eroded. To cope with this disadvantage, an O-ring 55 is disposed on the periphery of the shaft in the head in order to close the gap.

However, the O-ring 55 seals the gap in a manner being in contact with the shaft 52, and therefore driving of the shaft 52 can cause heat generation at the O-ring and wear-out of the same. In addition, a portion of the shaft 52 in contact with the O-ring 55 can wear as well. Therefore, the sealing performance of the O-ring can be deteriorated with the lapse of time, and further the durability of the O-ring and the shaft member can be damaged.

SUMMARY OF THE INVENTION

It is therefore an object of the present invention to provide a prophy head which is capable of preventing intrusion of contaminants into a head portion thereof and includes a dust control mechanism which is good in durability, for preventing the intrusion of contaminants. The above and other objects of the present invention will become more apparent from the following description.

According to the present invention, there is provided a prophy head comprising a shaft for holding a polishing member, a bearing for supporting the shaft, housing means for retaining the bearing, driving-force transmitting means for transmitting driving force to the shaft to rotate the shaft, and rotary dust control means rotating integrally with the shaft for preventing intrusion of contaminants through a gap between an inner surface of a lower end of the housing means and an outer periphery of the shaft, wherein said rotary dust control means has a surface extending radially outwardly from said outer periphery of the shaft and placed downwardly beyond said lower end of the housing means, and a surface placed in close proximity with said inner surface of the lower end of the housing means.

The prophy head according to the present invention has the rotary dust control means rotating integrally with the shaft, for preventing intrusion of contaminants into the head portion through the gap between the outer periphery of the shaft for rotating the polishing member and the inner surface of the lower end of the housing means including a mouthpiece or the like.

The rotary dust control means has a surface which extends radially outwardly from the outer periphery of the shaft and is placed downwardly beyond the lower end of the housing means, and a which is placed in close proximity with the inner surface of the lower end of the housing means. The surface of the rotary dust control means which is placed in close proximity with the inner surface of the lower end of the housing means is out of contact therewith.

The rotary dust control means constructed as above rotates integrally with the shaft, to thereby blow away contaminants in a radially outward direction of the shaft, more specifically in a tangential direction of the shaft. Therefore, the intrusion of contaminants through the contaminant intrusion port into the head portion can be prevented. Downward protrusion of the rotary dust control means to place its surface downwardly beyond the lower end of the housing means may assume a very small length insofar as the blown contaminants can be prevented from directing toward and entering the intrusion port. In addition, the rotary dust control means may be formed separately from the shaft, or formed integrally with the shaft by allowing part of the shaft to protrude radially outwardly from the same.

The rotary dust control means may be designed to have a collar portion, of which surface define an extension of the radially extending surface placed downwardly beyond the lower end of the housing means, so that a surface of the collar portion further extends radially outwardly to cover at least partly the lower end of the housing means. In this design, the contaminant intrusion port is covered with the collar portion in a manner being out of contact therewith. As a result, the intrusion of contaminants can be prevented more effectively, and a contaminant blowing effect can be more enhanced by centrifugal force of the collar portion.

The polishing member generally includes a polishing brush, a rubber cup, or the like. The prophy heads are broadly divided into a screw type in which the polishing brush is screwed into the shaft, and a knob type in which the rubber cup is installed on the knob portion of the shaft in a manner covering the same.

The bearing is usually a metal bearing, but it may be a ball bearing as well. The housing means includes the mouthpiece which is detachably connected to the lower end of the head portion.

According to the present invention, the prophy head may optionally has an additional stationary dust control means for further preventing intrusion of contaminants into the head portion so that a space of a depression defined by the rotary dust control means, the shaft, and the bearing is almost filled with the stationary dust control means without contacting with the surfaces of the rotary dust control means and the shaft defining the space. The stationary dust control means may be fixed to the lower portion of the bearing. It may be formed of a separate member and attached to the bearing, or alternatively formed by allowing part of the bearing to protrude downwardly.

PREFERRED EMBODIMENT OF THE PRESENT INVENTION

The present invention will now be described in detail with reference to the drawings showing preferred embodiments of the invention.

Figure 1:
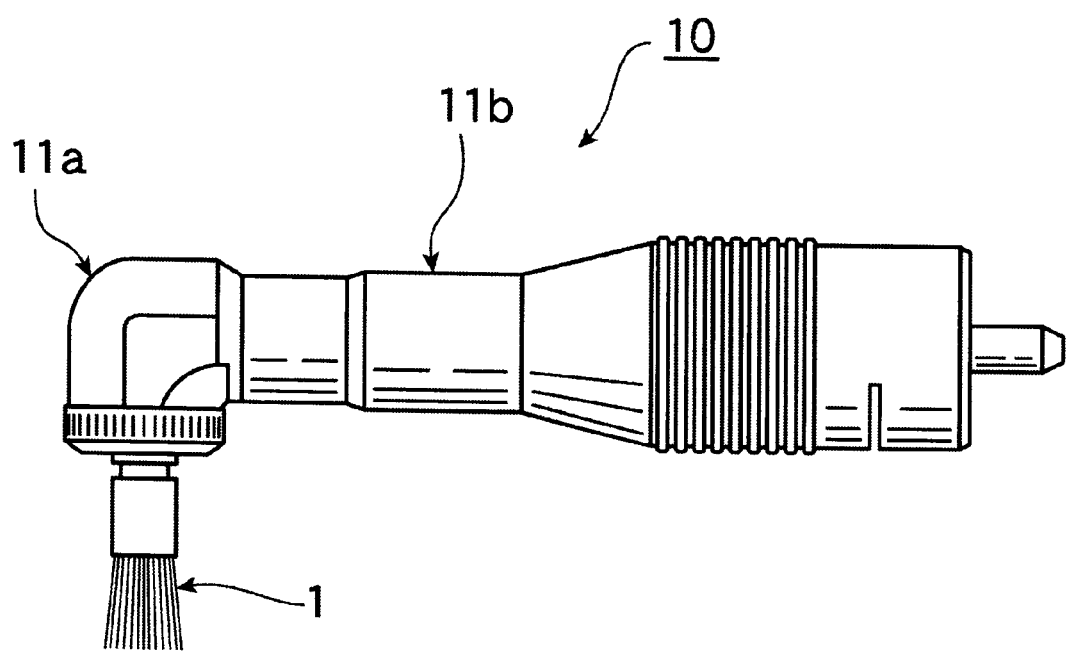
FIG. 1 is a side view showing the appearance of a screw type prophy head according to an embodiment of the invention.
Figure 2:
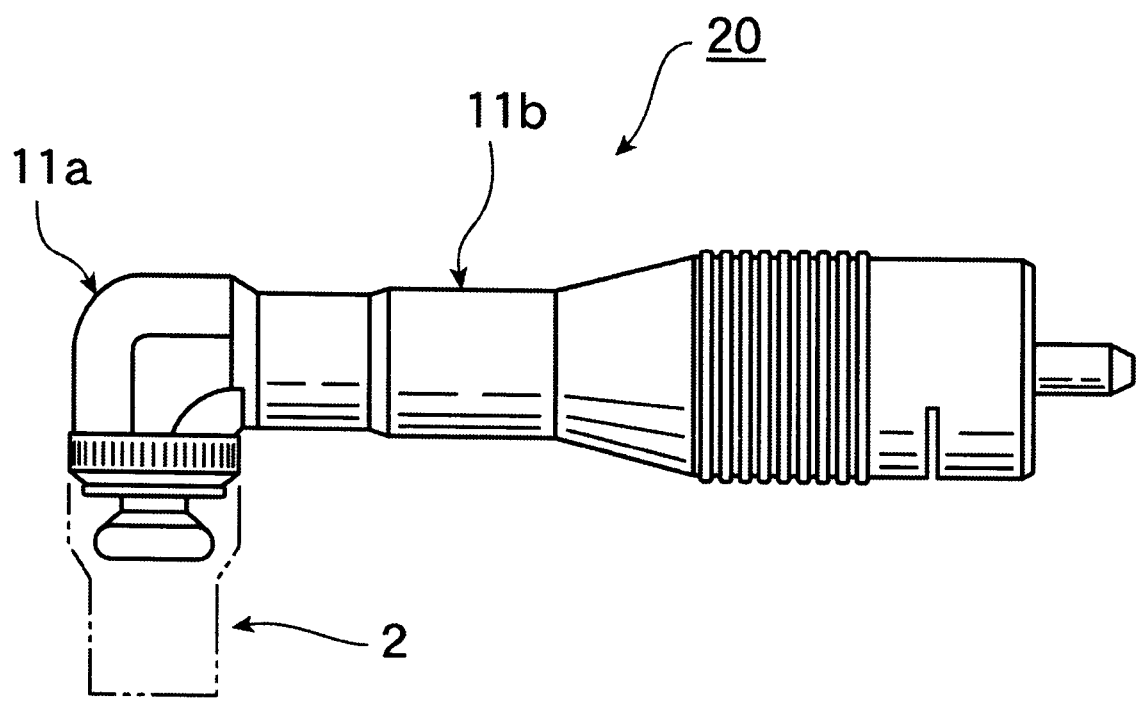
FIG. 2 is a partially cutaway side view showing the appearance of a knob type prophy head according to another embodiment of the invention.

FIGS. 1 and 2 are side views each showing the appearance of a prophy head designated by reference numerals 10 and 20, respectively, according to the invention. The prophy head 10, 20 has a head portion 11a and a neck portion 11b. To a lower portion of the head portion 11a is attached either a brush 1 or a rubber cup 2 as a polishing member. The neck portion 11b has its rear end connected to a sheath, not shown, in which a motor, a reduction gear, and the like as a driving source are accommodated.

Figure 3:
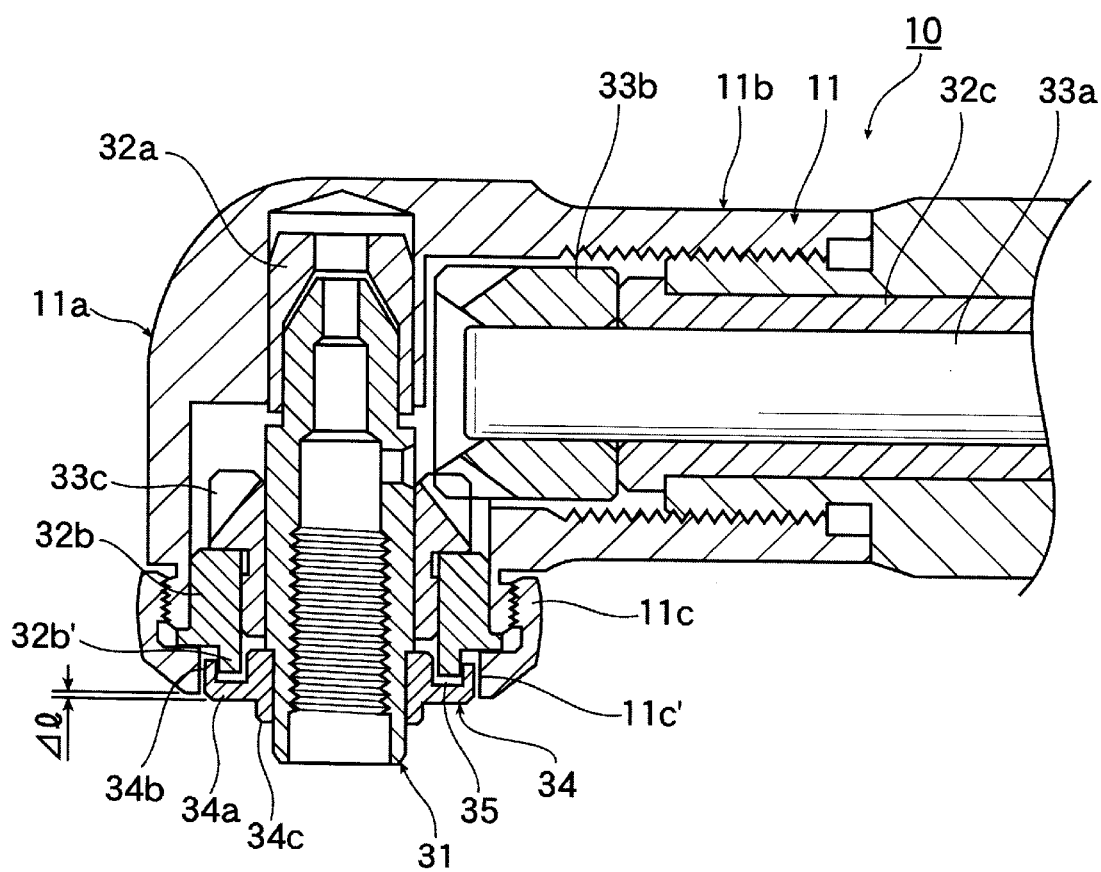
FIG. 3 is a partially elevated sectional view showing the construction of part of the prophy head shown in FIG. 1.
Figure 4:
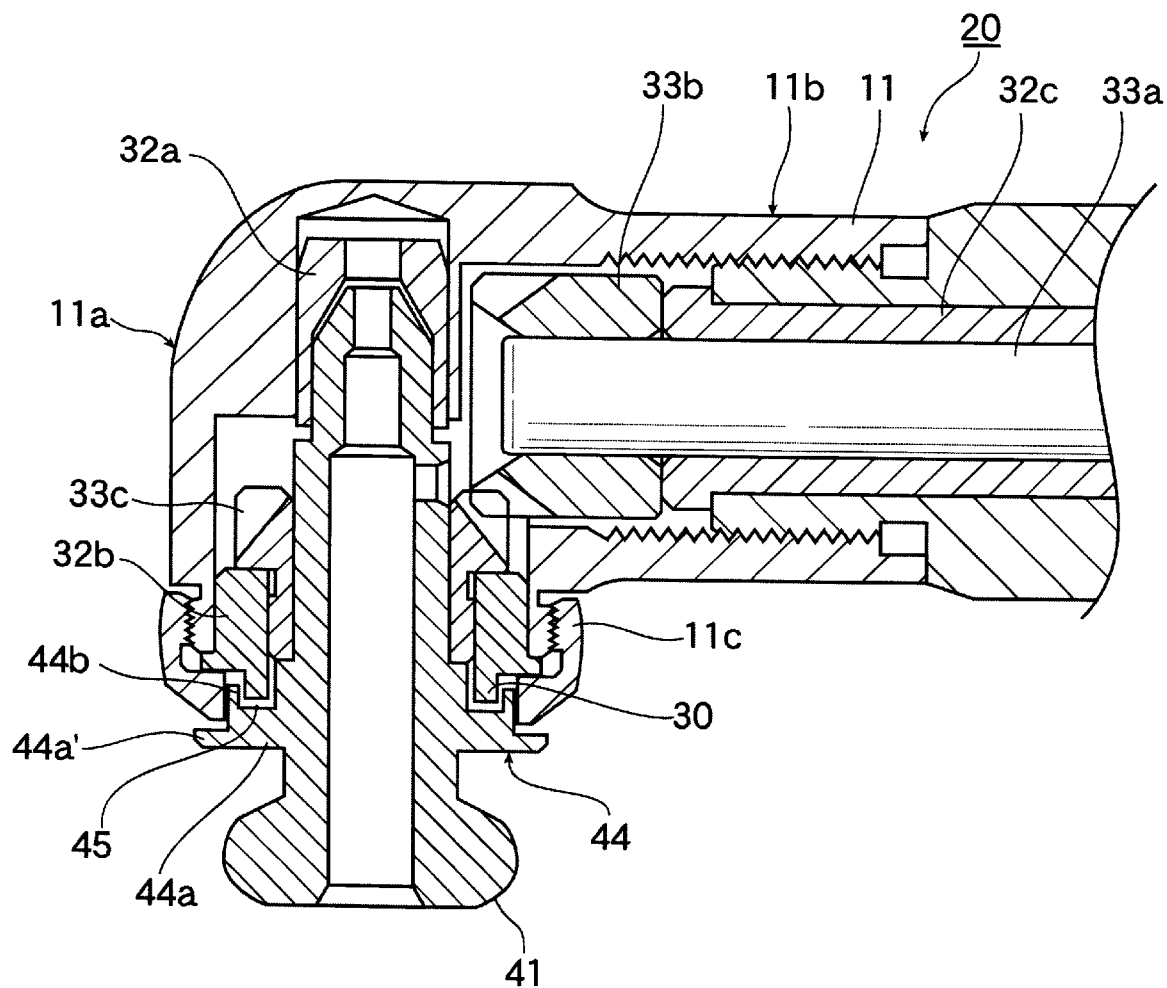
FIG. 4 is a partially elevated sectional view showing the construction of part of the prophy head shown in FIG. 2.
Figure 5:
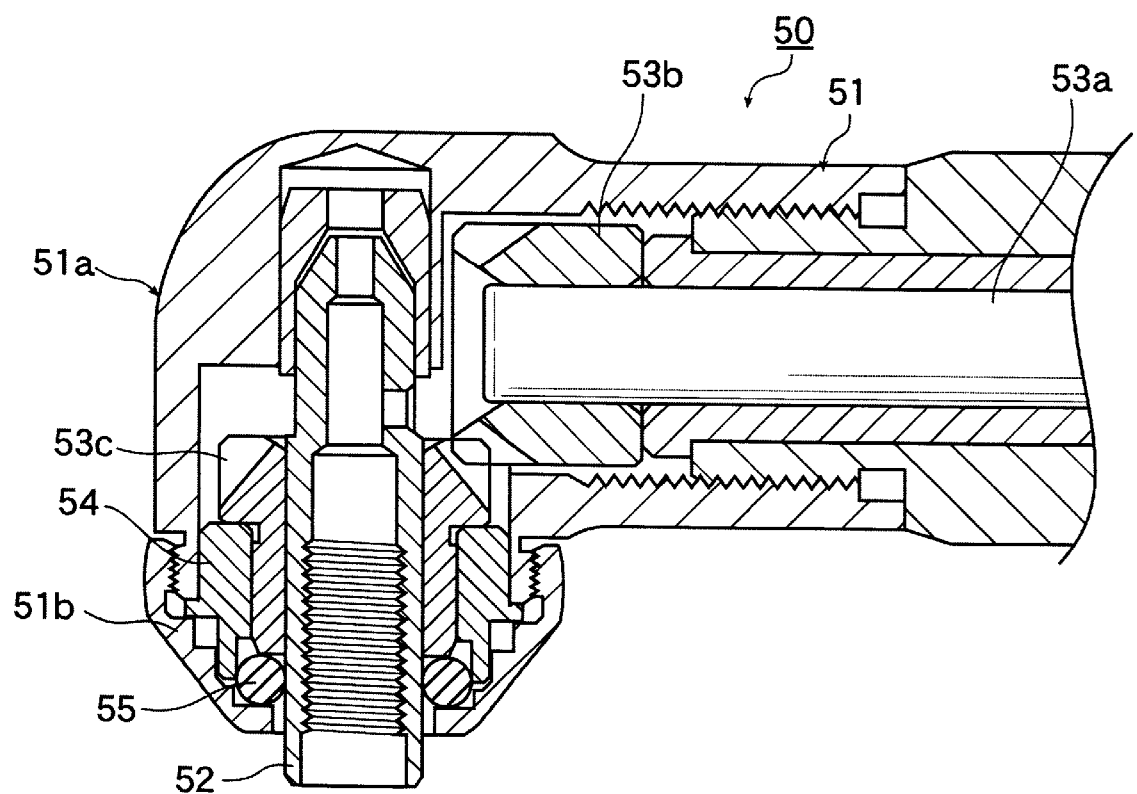
FIG. 5 is a cross sectional view showing the construction of a conventional prophy head.

FIG. 3 is a partially elevated sectional view showing the construction of part of the prophy head 10 shown in FIG. 1 after removing the brush 1 therefrom. On the other hand, FIG. 4 is a partially elevated sectional view showing the construction of part of the prophy head shown in FIG. 2 after removing the rubber cup 2 therefrom.

In FIG. 3, a housing section 11 of the prophy head 10 is composed of the head portion 11a, the neck portion 11b, and a mouthpiece 11c. The head portion 11a accommodates and securely holds therein upper and lower metal bearings 32a, 32b, which rotatably support a screw shaft 31. The head portion 11a forming the housing section 11 has a lower end, onto which is detachably screwed the mouthpiece 11c. The mouthpiece 11c and the head portion 11a retain the bearing 32b. The lower surface of the mouthpiece 11c defines the lower end of the housing section 11.

The neck portion 11b of the housing section 11 accommodates therein a driving shaft 33a arranged perpendicular to the screw shaft 31, and a metal bearing 32c rotatably supporting the driving shaft 33a. The driving shaft 33a has a front end at which a driving gear 33b is rigidly secured, and an output shaft gear 33c in mesh with the driving gear 33b is rigidly secured to the screw shaft 31. The driving shaft 33a, the driving gear 33b, the output shaft gear 33c, and the like form driving force transmitting means.

The prophy head 10 of the invention is provided with rotary dust control means described hereinbelow. Secured in a gap between the inner surface 11c' of the lower end of the mouthpiece 11c and the outer periphery of the screw shaft 31 facing to the inner surface 11c' is a rotary dust control disk 34 which is rotated together with the screw shaft 31 in a manner being out of contact with the inner surface 11c' and being in contact with the outer periphery of the screw shaft 31. The rotary dust control disk 34 has an annular flange portion 34a extending radially outwardly from the screw shaft 31, and an annular bent portion bent upward from the outer periphery of the flange portion 34a. The flange portion 34a and the bent portion 34b are formed integrally to have an L-shaped cross section, on the outer periphery of the screw shaft 31 via a disk base portion 34c. In order to receive the rotary dust control disk 34, the gap between the outer periphery of the screw shaft 31 and the inner surface 11c' of the lower end of the mouthpiece 11c is more enlarged than in a conventional prophy head.

The flange portion 34a, the bent portion 34b, and the disk base portion 34c cooperatively forming the rotary dust control disk 34 define an annular depression 35 shown in FIG. 3. The lower surface of the flange portion 34a below the depression 35 is placed slightly downwardly beyond the lower surface of the mouthpiece 11c by $\Delta 1$ as shown in FIG. 3.

The metal bearing 32b is provided with a fixed disk 32b' of an annular shape, which protrudes downward from the bearing 32b to be received in the depression 35. The fixed disk 32b' may be integrally formed with the metal bearing 32b such that part of the metal bearing 32b protrudes, or alternatively it may be formed as a member separate from the bearing. FIG. 3 shows the former embodiment. This fixed disk 32b' functions as stationary dust control means.

Next, description will be made of a manner of use of the prophy head 10 constructed as above. First, when the motor in the sheath to which the prophy head 10 is connected is driven, an output from the motor is decelerated to approximately 2000 rpm by the reduction gear accommodated in the sheath. Then, the output from the motor is transmitted via the driving shaft 33a, the driving gear 33b, and the output shaft gear 33c to the screw shaft 31, and the thus transmitted output rotates the brush 1, to thereby carry out required polishing work. At this time, the rotary dust control disk 34 is rotated together with the shaft 31. The dust control disk 34 thus rotated is arranged such that the lower surface of the flange portion 34a is placed slightly downwardly beyond the lower surface of the mouthpiece 11c, and therefore the disk 34 functions to blow away dust and the like around the rotary dust control disk 34 in a radially outward direction of the screw shaft 31. In this manner, contaminants can be prevented from entering the interior of the head portion through the minute gap (contaminant intrusion port) formed between the rotary dust control disk 34 and the mouthpiece 11c.

Further, the fixed disk 32b' arranged in the depression 35 of the rotary dust control disk 34 in close proximity with, but out of contact with the disk 34, partitions a space spreading from the minute gap formed between the rotary dust control disk 34 and the mouthpiece 11c to the output shaft gear 33c in a manner shown in FIG. 3. Therefore, the fixed disk 32b' forms a kind of a labyrinth structure and accordingly functions as stationary dust control means. The prophy head 10 having the construction as above can prevent entering of contaminants into the above space in a more effective manner.

Next, description will be made of another embodiment of the present invention, with reference to FIG. 4. FIG. 4 is a partially elevated sectional view showing the construction of the knob-type prophy head 20 in which the rubber cup 2 as the polishing member is installed on a knob shaft 41 for rotating the polishing member. In FIG. 4, elements and parts which are identical with those in FIG. 3 are designated by identical reference numerals in FIG. 3, description thereof being omitted.

The rotary dust control disk 44 installed on the knob shaft 41 of the prophy head 20 is provided with a flange portion 44a which is thicker than that of the rotary dust control disk 34 shown in FIG. 3, and a bent portion 44b, to thereby form a depression 45 similar to the depression 35 in FIG. 3. Further, the rotary dust control disk 44 has a collar portion 44a' extending radially outwardly from the knob shaft 41 in a manner approaching the lower surface of the mouthpiece 11c to cover the contaminant intrusion port. The knob shaft 41 and the rotary dust control disk 44 may be formed integrally, or alternatively they may be separately formed. FIG. 4 shows the former embodiment. In addition, the length of the collar portion 44a' extending radially outwardly from the knob shaft 41 is not particularly limited, but it is desirable that the collar portion 44a' assumes a length shown in FIG. 4.

In the prophy head 20, since the collar portion 44a' extends radially outwardly from the knob shaft 41, centrifugal force caused by rotation of the collar portion 44a' enhances the effect of blowing away contaminants such as dust. In addition, the collar portion 44a' is constructed so as to cover the contaminant intrusion port in a fashion being out of contact therewith, and therefore it can prevent contaminants from entering the interior of the head portion in a further positive manner. In regard of this point, the collar portion 44a' like this may be provided on the rotary dust control disk 34 shown in FIG. 3.

As described hereinabove, according to the prophy head of the present invention, non-contact type dust control means having a rotary member and the like is provided, rotational resistance, heat generation, and therefore abrasion of a dust control mechanism are conspicuously reduced compared to a conventional dust control mechanism using an O-ring, whereby durability of the mechanism is improved. In addition, the deletion of the O-ring enables the shape of a head portion of the prophy head to be more compact. As a result, for instance, when the prophy head of the invention is used in the oral cavity of a patient, field of view of a person operating the prophy head can be advantageously enlarged.

While there has been described what are at present considered to be preferred embodiments of the invention, it will be understood that various modifications may be made thereto, and it is intended that the appended claims cover all such modifications as fall within the true spirit and scope of the invention.

What is claimed is:

1. A prophy head comprising:
   a shaft for holding a polishing member;
   a bearing for supporting said shaft;
   a housing for retaining said bearing;
   a driving-force transmitter for transmitting driving force to said shaft to rotate said shaft; and
   a rotary dust controller provided on and rotating integrally with the shaft for preventing intrusion of contaminants through a gap between an inner surface of a lower end of said housing and an outer periphery of the shaft;
   wherein said rotary dust controller has a surface extending radially outwardly from said outer periphery of the shaft and placed downwardly beyond said lower end of the housing and a surface placed facing inner surface of the lower end of the housing and forming a gap there between.

2. The prophy head of claim 1 wherein said surface of the rotary dust controller extending radially outwardly from the outer periphery of the shaft and placed downwardly beyond the lower end of the housing extends to cover the lower end of the housing.

3. The prophy head of claim 2 further comprising a stationary dust controller provided integrally with said bearing at a lower portion of said bearing, said stationary dust controller almost filling a space formed between the shaft and the rotary dust controller without contacting with surfaces of said shaft and the rotary dust controller defining said space.

4. The prophy head of claim 1 further comprising a stationary dust controller provided integrally with said bearing at a lower portion of said bearing, said stationary dust controller almost filling a space formed between the shaft and the rotary dust controller without contacting with surfaces of said shaft and the rotary dust controller defining said space.

* * * * *